United States Patent [19]
Lamm et al.

[11] Patent Number: 6,013,775
[45] Date of Patent: Jan. 11, 2000

[54] POLYAZO DYES CONTAINING A PLURALITY OF HYDROXY SULFONYL GROUPS

[75] Inventors: Gunther Lamm, Hassloch; Matthias Wiesenfeldt, Dannstadt-Schauernheim, both of Germany

[73] Assignee: BASF Aktiengesellschaft, Ludwigshafen, Germany

[21] Appl. No.: 08/959,033

[22] Filed: Oct. 28, 1997

[30] Foreign Application Priority Data

Nov. 26, 1996 [DE] Germany ............... 196 48 939

[51] Int. Cl.[7] .................. C09B 62/533; C09B 35/28; C09B 35/02; D06P 1/38
[52] U.S. Cl. .................. 534/642; 534/645; 534/796; 534/807; 534/816; 534/819
[58] Field of Search .................. 534/819, 816, 534/807, 634, 796, 642; 558/47, 48, 58; 562/65

[56] References Cited

U.S. PATENT DOCUMENTS

| | | | |
|---|---|---|---|
| 2,092,429 | 9/1937 | Straub et al. | 534/807 X |
| 2,154,248 | 4/1939 | Northey | 562/65 |
| 2,165,484 | 7/1939 | Huismann | 534/819 X |
| 2,184,515 | 12/1939 | Cliffe | 534/819 X |
| 2,258,162 | 10/1941 | Northey et al. | 562/65 |
| 2,944,050 | 7/1960 | Haubrich et al. | 534/819 X |
| 3,210,335 | 10/1965 | Zickendraht et al. | 558/48 |
| 3,657,218 | 4/1972 | Gnad | 534/819 X |
| 4,013,634 | 3/1977 | Stryker | 534/807 |
| 4,242,258 | 12/1980 | Noll et al. | 534/816 X |
| 4,479,906 | 10/1984 | Zeidler et al. | 534/816 X |
| 5,629,410 | 5/1997 | Deitz et al. | 534/642 |

FOREIGN PATENT DOCUMENTS

| | | | |
|---|---|---|---|
| 0559653 | 7/1958 | Canada | 534/819 |
| 0 716 130 | 6/1996 | European Pat. Off. . | |
| 2206359 | 6/1974 | France . | |
| 2 417 529 | 9/1979 | France . | |
| 24 15 690 | 10/1975 | Germany . | |
| 2539162 | 3/1977 | Germany | 534/819 |
| 387 842 | 2/1965 | Switzerland . | |
| 0482524 | 3/1938 | United Kingdom | 562/65 |

OTHER PUBLICATIONS

Chemical Abstracts, vol. 83, No. 24, Dec. 15, 1975, Columbus, Ohio, US; Abstract No. 195215t, A. Kotone et al.: "Tetrakisazo Dyes" Seite 116; XP002073885 *Zusammenfassung* & JP 50 034 029 A (Sakai Chemical Industry Co., Ltd.) Apr. 2, 1975 *Beispiel 1*.

Primary Examiner—Floyd D. Higel
Attorney, Agent, or Firm—Oblon, Spivak, McClelland, Maier & Neustadt, P.C.

[57] ABSTRACT

Polyazo dyes of the formula I

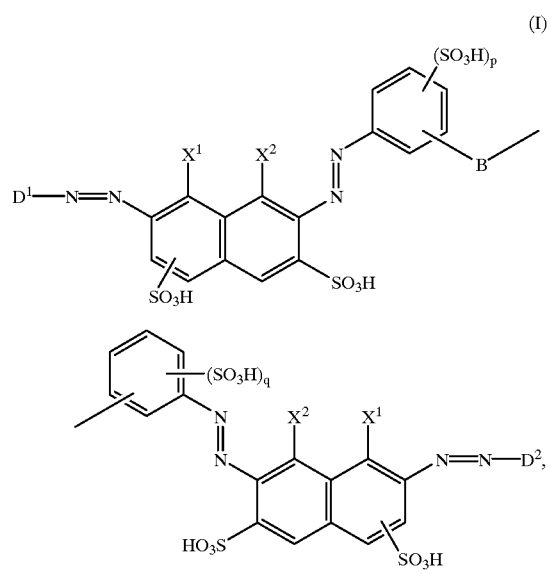

where one of the two radicals $X^1$ and $X^2$ is hydroxyl and the other is amino, p and q are each independently of the other 0 or 1, $D^1$ and $D^2$ are each independently of the other a radical of the formula

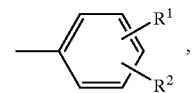

and B is a bridge member are prepared using novel sulfonamide intermediates and are useful as dyes for dyeing natural or synthetic substrates.

10 Claims, No Drawings

POLYAZO DYES CONTAINING A PLURALITY OF HYDROXY SULFONYL GROUPS

The present invention relates to polyazo dyes of the formula I

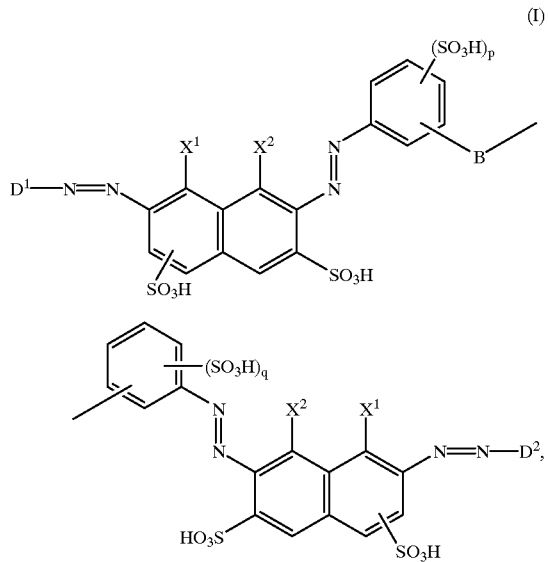

(I)

where one of the two radicals $X^1$ and $X^2$ is hydroxyl and the other is amino, p is 0 or 1, q is 0 or 1, $D^1$ and $D^2$ are each independently of the other a radical of the formula

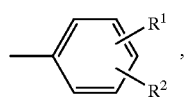

B is a bridge member of the formula

—$SO_2$—NH—$A^1$—NH—$SO_2$—, —$SO_2$—N(Alk)—$A^1$—NH—$SO_2$—,

—$SO_2$—N(Alk)—$A^1$—N(Alk)—$SO_2$—, —$SO_2$—N(Alk)—$A^1$—O—$SO_2$—,

—$SO_2$—O—$A^1$—O—$SO_2$—, —$SO_2$—N(Alk)—, —$SO_2$—N(Alk)—$SO_2$—,

—$SO_2$—NH—$A^2$—NH—$SO_2$—, —$SO_3$— or $SO_2$, where $A^1$ is phenylene with or without substitution by hydroxysulfonyl, $A^2$ is $C_1$–$C_8$-alkylene and $R^1$ is hydrogen, $C_1$–$C_4$-alkyl, halogen, cyano, nitro, hydroxysulfonyl, pyrrolidinylsulfonyl, piperidinylsulfonyl, morpholinylsulfonyl or a radical of the formula CO—Ar, CO—OAr, CO—Alk, CO—OAlk, CO—N(Ar)Alk, CO—N(Alk)$_2$, $SO_2$—Ar, $SO_2$—Alk, $SO_2$—$CH_2CH$=$CH_2$, $SO_2$—CH=$CH_2$, $SO_2$—$C_2H_4$—Q, $SO_2$—OAr, $SO_2$—N(Alk)$_2$, $SO_2$—NHAlk, $SO_2$—N(Ar)Alk, $SO_2$—NHAr,

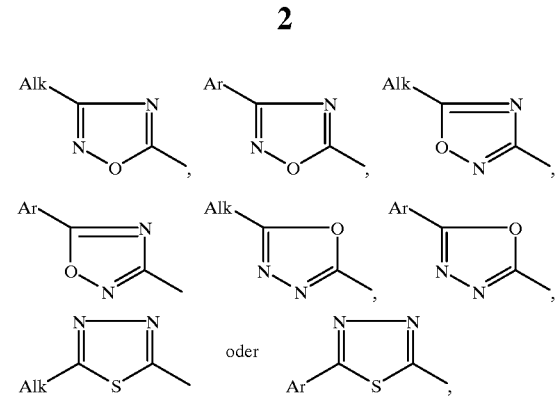

oder

Alk is $C_1$–$C_8$-alkyl with or without interruption by from 1 to 3 oxygen atoms in ether function or by 1 sulfur atom or one sulfonyl group and with or without hydroxyl, $C_1$–$C_4$-alkanoyloxy, benzoyloxy, sulfato, halogen, cyano, carbamoyl, carboxyl, hydroxysulfonyl, phenyl or hydroxysulfonylphenyl substitution, or $C_5$–$C_8$-cycloalkyl, Ar is phenyl or naphthyl, these radicals each being with or without substitution by $C_1$–$C_4$-alkyl, halogen, $C_1$–$C_4$-alkoxy, phenoxy, hydroxyl, carboxyl, $C_1$–$C_4$-alkanoylamino whose alkyl chain is with or without interruption by one oxygen atom in ether function, benzoylamino, hydroxysulfonyl, pyrrolidinylsulfonyl, piperidinylsulfonyl, morpholinylsulfonyl or a radical of the formula $SO_2$—Alk, $SO_2$—$CH_2CH$=$CH_2$, $SO_2$—CH=$CH_2$, $SO_2$—$C_2H_4$—Q, $SO_2$—NHAlk, $SO_2$—N(Alk)$_2$, $SO_2$—G, $SO_2$—OG, $SO_2$—NHG or $SO_2$—N(Alk)G, $R^2$ is hydrogen, hydroxysulfonyl, $C_1$–$C_4$-alkyl, $C_1$–$C_4$-alkoxy or a radical of the formula CO—Ar, CO—OAlk, CO—OAr, $SO_2$—Ar, $SO_2$—Alk, $SO_2$—OAr,

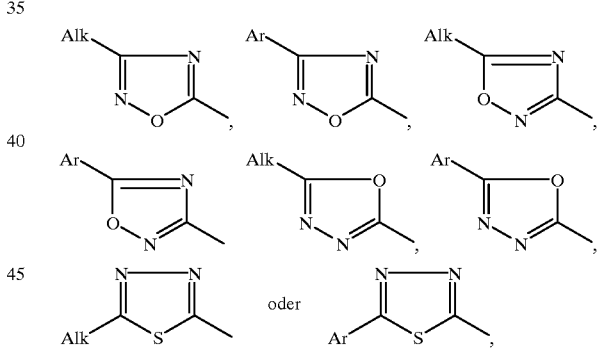

oder

Q is hydroxyl or an alkali-detachable group, and

G is phenyl with or without $C_1$–$C_4$-alkyl, carboxyl, hydroxysulfonyl or $C_1$–$C_4$-alkanoylamino substitution, or naphthyl with or without hydroxysulfonyl substitution, sulfonamides as intermediates therefor and the use of the novel dyes for dyeing natural or synthetic substrates.

EP-A 716 130 describes fiber-reactive azo dyes formed from 4-(γ-sulfatoethylsulfonyl)aniline and H-acid and doubled via their naphthalene structure with diazotized bis(p-aminobenzenesulfon)imide or diazotized p,p'-diaminobenzenesulfanilide. However, textiles dyed with these dyes are observed to have changed in color after a wash.

It is an object of the present invention to provide novel polyazo dyes having advantageous application properties, especially high color strength coupled with good fastnesses.

We have found that this object is achieved by the polyazo dyes of the formula I defined at the outset.

Any alkyl appearing in the abovementioned formula I may be straight-chain or branched.

Substituted alkyl appearing in the abovementioned formula generally has 1 or 2 substituents.

Alkyl in the abovementioned formulae which is interrupted by oxygen atoms in ether function is preferably alkyl interrupted by 1 or 2 oxygen atoms in ether function.

Substituted phenyl appearing in the abovementioned formulae generally has from 1 to 3 substituents.

Substituted phenylene generally has 1 or 2, preferably one, hydroxysulfonyl radical.

$A^1$ is preferably 1,2-, 1,3- or 1,4-phenylene, 2-hydroxysulfonyl-1,3-phenylene, 2-hydroxysulfonyl-1,4-phenylene or 2,5-dihydroxysulfonyl-1,4-phenylene.

$A^2$ and $A^3$, which is mentioned below, are each for example $CH_2$, $(CH_2)_2$, $(CH_2)_3$, $(CH_2)_4$, $CH(CH_3)CH_2$, $CH(CH_3)CH(CH_3)$, $(CH_2)_5$, $(CH_2)_6$, $(CH_2)_7$ or $(CH_2)_8$.

$R^1$, $R^2$ and Alk are each for example methyl, ethyl, propyl, isopropyl, butyl, isobutyl, sec-butyl or tert-butyl.

$R^1$ and halogen may also be for example fluorine, chlorine or bromine.

$R^2$ may also be for example methoxy, ethoxy, propoxy, isopropoxy, butoxy, isobutoxy, sec-butoxy or tert-butoxy.

Alk may also be for example pentyl, isopentyl, neopentyl, tert-pentyl, hexyl, 2-methylpentyl, heptyl, 1-ethylpentyl, octyl, 2-ethylhexyl, isooctyl (The above designation isooctyl is a trivial name derived from the alcohols obtained by the oxo process—cf. Ullmann's Encyclopedia of Industrial Chemistry, 5th Edition, Vol. A 1, pages 290 to 293, and also Vol. A 10, pages 284 and 285), 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 3,6,9-trioxadecyl, 3,6,9-trioxaundecyl, 2-methylthioethyl, 2-ethylthioethyl, 2- or 3-methylthiopropyl, 2- or 3-ethylthiopropyl, 2- or 4-methylthiobutyl, 2- or 4-ethylthiobutyl, 2-methylsulfonylethyl, 2-ethylsulfonylethyl, 2- or 3-methylsulfonylpropyl, 2- or 3-ethylsulfonylpropyl, 2- or 4-methylsulfonylbutyl, 2- or 4-ethylsulfonylbutyl, chloromethyl, 2-chloroethyl, 2- or 3-chloropropyl, benzyl, 1- or 2-phenylethyl, 2-, 3- or 4-hydroxysulfonylbenzyl, 2-(2-, 3- or 4-hydroxysulfonylphenyl)ethyl, 3-benzyloxypropyl, 2-hydroxyethyl, 2- or 3-hydroxypropyl, cyanomethyl, 2-cyanoethyl, 2- or 3-cyanopropyl, carbamoylmethyl, 2-carbamoylethyl, 2- or 3-carbamoylpropyl, 2-acetyloxyethyl, 2- or 3-acetyloxypropyl, 2-isobutyryloxyethyl, 2- or 3-isobutyryloxypropyl, carboxylmethyl, 2-carboxylethyl, 2- or 3-carboxylpropyl, 2-hydroxysulfonylethyl, 2- or 3-hydroxysulfonylpropyl, 2-sulfatoethyl, 2- or 3-sulfatopropyl, cyclopentyl, cyclohexyl, cycloheptyl or cyclooctyl.

Ar is for example phenyl, 2-, 3- or 4-methylphenyl, 2-, 3- or 4-ethylphenyl, 2-, 3- or 4-propylphenyl, 2-, 3- or 4-isopropylphenyl, 2-, 3- or 4-butylphenyl, 2,4-dimethylphenyl, 2-, 3- or 4-phenoxyphenyl, 2-, 3- or 4-hydroxyphenyl, 2-, 3- or 4-methoxyphenyl, 2-, 3- or 4-ethoxyphenyl, 2-, 3- or 4-isobutoxyphenyl, 2,4-dimethoxyphenyl, 2-, 3- or 4-formylaminophenyl, 2-, 3- or 4-acetylaminophenyl, 2-, 3- or 4-propionylaminophenyl, 2-, 3- or 4-methoxyacetylaminophenyl, 2-, 3- or 4-chlorophenyl, 2-, 3- or 4-carboxyphenyl, 2-, 3- or 4-hydroxysulfonylphenyl, 2-, 3- or 4-benzoylaminophenyl, 2-, 3- or 4-pyrrolidinylsulfonylphenyl, 2-, 3- or 4-piperidinesulfonylphenyl, 2-, 3- or 4-morpholinylsulfonylphenyl, 2-, 3- or 4-methylsulfonylphenyl, 2-, 3- or 4-carboxymethylsulfonylphenyl, 2-, 3- or 4-vinylsulfonylphenyl, 2-, 3- or 4-(2-hydroxyethyl)sulfonylphenyl, 2-, 3- or 4-(2-sulfatoethyl)sulfonylphenyl, 2-, 3- or 4-ethylsulfamoylphenyl, 2-, 3- or 4-(2-hydroxyethyl)sulfamoylphenyl, 2-, 3- or 4-bis(2-hydroxyethyl)sulfamoylphenyl, naphth-1-yl, naphth-2-yl, 2-hydroxysulfonylnaphth-1-yl, 5-hydroxysulfonylnaphth-1-yl or 5-hydroxysulfonylnaphth-2-yl.

Q is hydroxyl or an alkali-detachable group. Examples of such groups are chlorine, bromine, $C_1$–$C_4$-alkylsulfonyl, phenylsulfonyl, $OSO_3H$, $SSO_3H$, $OP(O)(OH)_2$, $C_1$–$C_4$-alkylsulfonyloxy, phenylsulfonyloxy, $C_1$–$C_4$-alkanoyloxy, $C_1$–$C_4$-dialkylamino, cyanamino or a radical of the formula

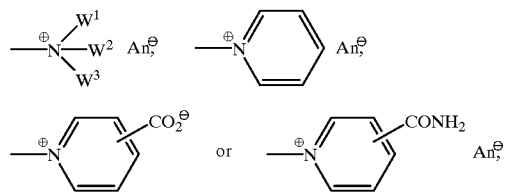

where $W^1$, $W^2$ and $W^3$ are each independently of the others $C_1$–$C_4$-alkyl or benzyl and An$\theta$ is in each case one equivalent of an anion. Examples of suitable anions are fluoride, chloride, bromide, iodide, mono-, di- or trichloroacetate, methylsulfonate, phenylsulfonate or 2- or 4-methylphenylsulfonate.

$R^1$ and $R^2$ are each for example benzoyl, 2-, 3- or 4-methylbenzoyl, 2,3-, 2,4-, 2,5-, 2,6-, 3,4- or 3,5-dimethylbenzoyl, methoxycarbonyl, ethoxycarbonyl, propoxycarbonyl, isopropoxycarbonyl, butoxycarbonyl, methylsulfonyl, ethylsulfonyl, propylsulfonyl, isopropylsulfonyl, butylsulfonyl, 5-methyl-, 5-ethyl-, 5-propyl-, 5-butyl- or 5-phenyl-1,2,4-oxadiazol-3-yl, 5-methyl-, 5-ethyl-, 5-propyl-, 5-butyl- or 5-phenyl-1,3,4-oxadiazol-2-yl, 3-methyl-, 3-ethyl-, 3-propyl-, 3-butyl- or 3-phenyl-1,2,4-oxadiazol-5-yl, phenylsulfonyl, 2-, 3- or 4-methylphenylsulfonyl, 2,3-, 2,4-, 2,5-, 2,6-, 3,4- or 3,5-dimethylphenylsulfonyl, phenoxycarbonyl, 2-, 3- or 4-methylphenoxycarbonyl, phenoxysulfonyl or 2-, 3- or 4-methylphenoxysulfonyl.

$R^1$ may also be for example N-phenyl-N-methylsulfamoyl, N-phenyl-N-ethylsulfamoyl, N-phenyl-N-propylsulfamoyl, N-phenyl-N-butylsulfamoyl, phenylsulfamoyl, 2-, 3- or 4-methylphenylsulfamoyl, dimethylsulfamoyl, diethylsulfamoyl, dipropylsulfamoyl, dibutylsulfamoyl, N-methyl-N-ethylsulfamoyl, bis(2-hydroxyethyl)sulfamoyl, bis(carboxymethyl)sulfamoyl, bis(2-carboxyethyl)sulfamoyl, methylsulfamoyl, ethylsulfamoyl, propylsulfamoyl, isopropylsulfamoyl, butylsulfamoyl, 2-hydroxyethylsulfamoyl, carboxymethylsulfamoyl, 2-carboxyethylsulfamoyl, dimethylcarbamoyl, diethylcarbamoyl, dipropylcarbamoyl, dibutylcarbamoyl, N-methyl-N-ethylcarbamoyl, bis(2-hydroxyethyl)carbamoyl, bis(carboxymethyl)carbamoyl, bis(2-carboxyethyl)carbamoyl, N-phenyl-N-methylcarbamoyl, N-phenyl-N-ethylcarbamoyl, N-phenyl-N-propylcarbamoyl, N-phenyl-N-butylcarbamoyl, 2-hydroxyethylsulfonyl, 2-chloroethylsulfonyl, 2-sulfatoethylsulfonyl or 2-acetyloxyethylsulfonyl.

$D^1$ and $D^2$ may be different within one and the same molecule and thus bear different substituents $R^1$ and also different substituents $R^2$.

The radicals
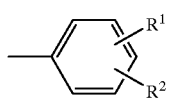
conform for example to the formulae
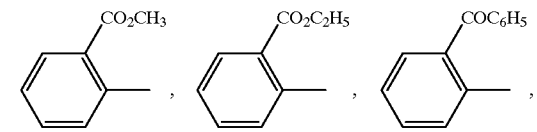
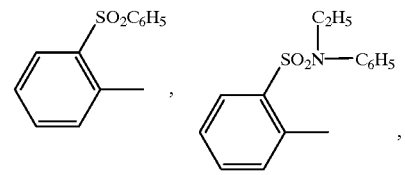
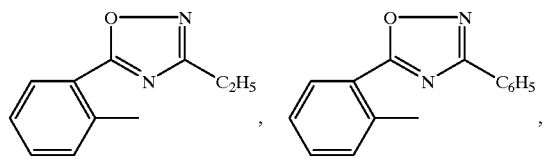
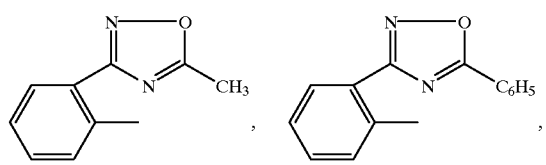
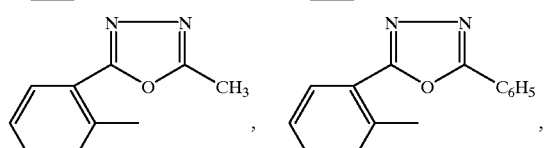
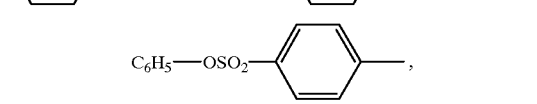
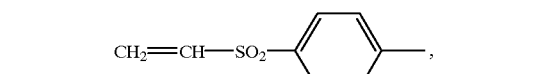
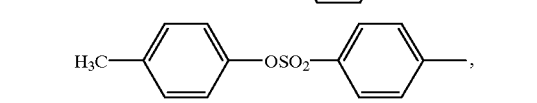
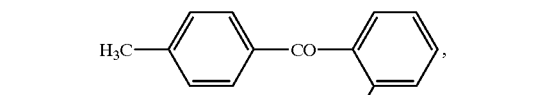
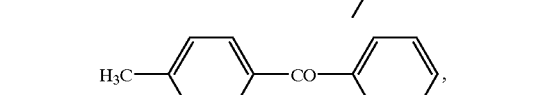
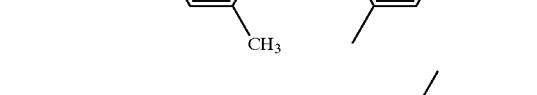
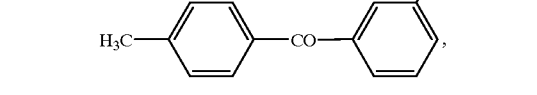
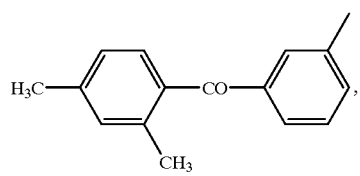
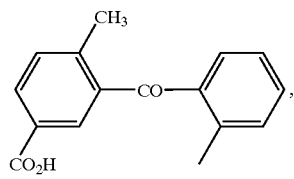
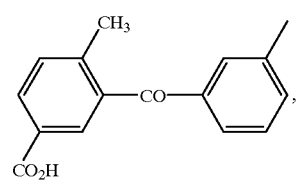
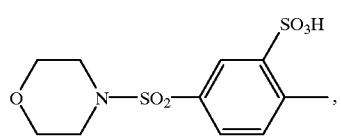
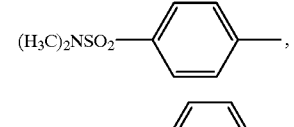
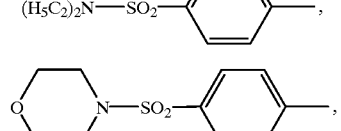
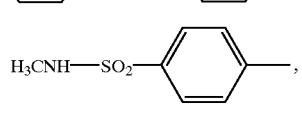
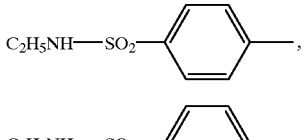
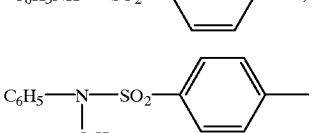
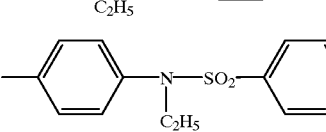
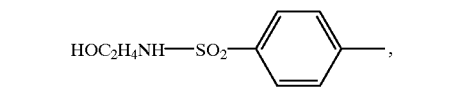
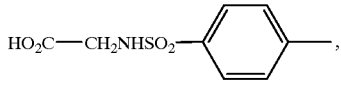

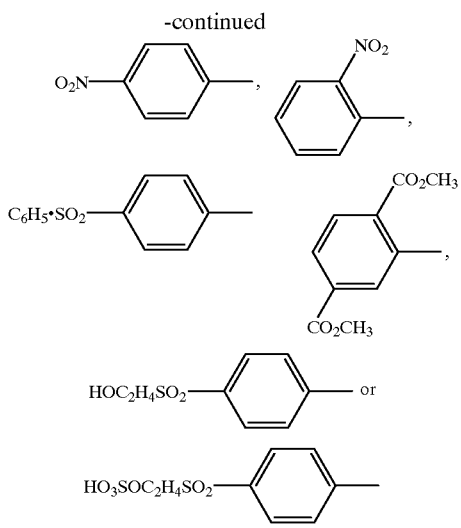

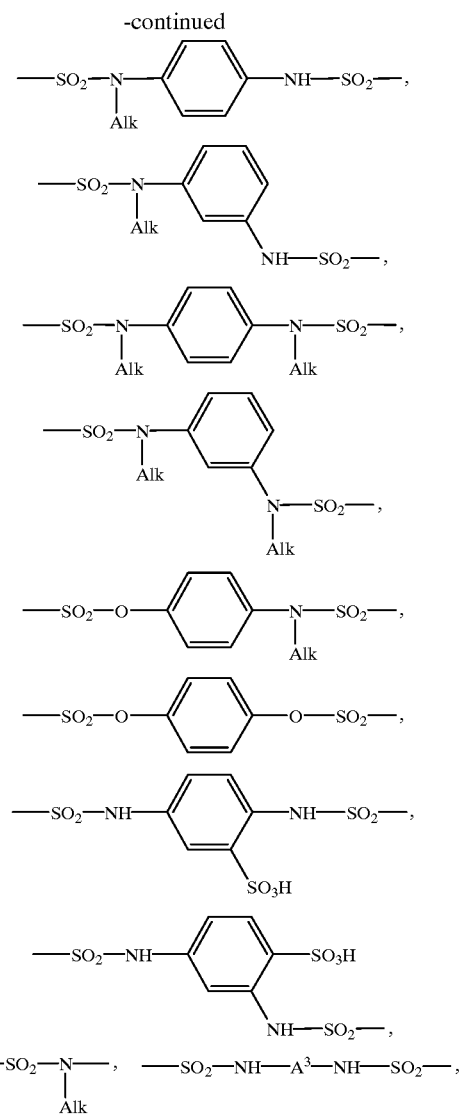

Since the disazo dyes of the formula I contain a plurality of hydroxysulfonyl groups and optionally also carboxyl groups, their salts are also encompassed by the invention.

Suitable salts are metal or ammonium salts. Metal salts are in particular lithium, sodium or potassium salts. Ammonium salts for the purposes of the present invention are salts having substituted or unsubstituted ammonium cations. Examples of the substituted ammonium cations are monoalkyl-, dialkyl-, trialkyl-, tetraalkyl- or benzyltrialkyl-ammonium cations or those cations derived from nitrogenous five- or six-membered saturated heterocycles, such as pyrrolidinium, piperidinium, morpholinium or piperazinium cations or their N-monoalkyl- or N,N-dialkylsubstituted products. Alkyl is generally straight-chain or branched $C_1$–$C_{20}$-alkyl with or without substitution by from 1 to 3 hydroxyl groups and/or with or without interruption by from 1 to 4 oxygen atoms in ether function.

Preference is given to polyazo dyes of the formula I where p and q are each 0.

Preference is further given to polyazo dyes of the formula I where Alk is $C_1$–$C_6$-alkyl with or without interruption by one or two oxygen atoms in ether function or by one sulfonyl group and with or without hydroxyl, $C_1$–$C_4$-alkanoyloxy, sulfato, chlorine, cyano, carboxyl, hydroxysulfonyl, phenyl or hydroxysulfonylphenyl substitution.

Preference is further given to polyazo dyes of the formula I where Ar is phenyl with or without substitution by $C_1$–$C_4$-alkyl, $C_1$–$C_4$-alkoxy, carboxyl, $C_1$–$C_4$-alkanoylamino, methoxyacetylamino, hydroxysulfonyl or a radical of the formula $SO_2$—$CH$=$CH_2$, $SO_2$—$C_2H_4$—Q, $SO_2$—NHAlk, $SO_2$—N(Alk)$_2$, $SO_2$—G, $SO_2$—OG, $SO_2$—NHG or $SO_2$—N(Alk) G.

The bridge members B conform for example to the formulae

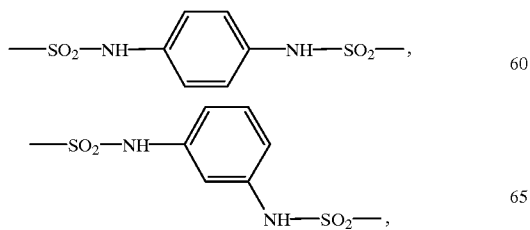

where $A^3$ is $C_1$–$C_6$-alkylene and Alk is as defined above. Bridge members having the preferred Alk radicals are particularly preferred.

Particularly preferred Alk is $C_1$–$C_6$-alkyl with or without interruption by 1 or 2 oxygen atoms or 1 sulfonyl group and with or without substitution by hydroxyl, $C_1$–$C_4$-alkanoyloxy, sulfato, carboxyl or hydroxysulfonyl. In bridge members bearing two Alk radicals, the radicals can be identical or different, for example

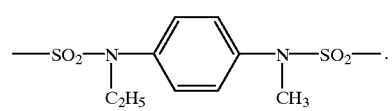

Specific examples of bisamino compounds from which the bridge members are derived are:

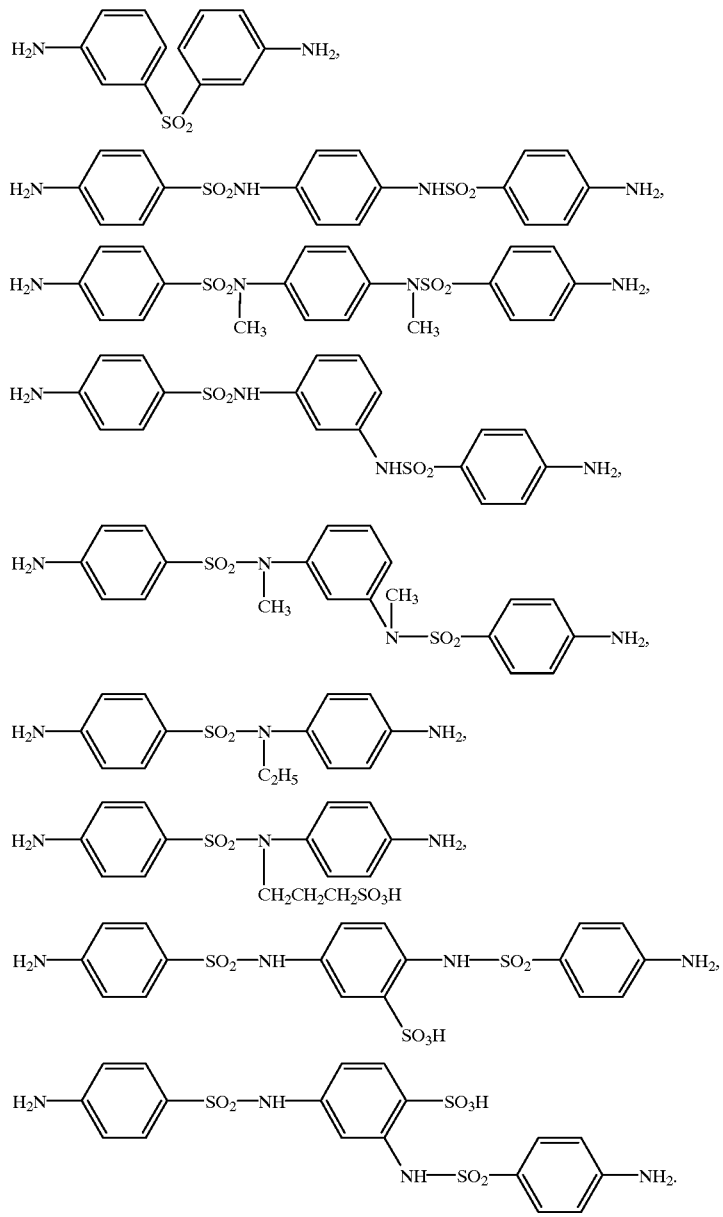

Preference is given to polyazo dyes having a phenylene (bisamino sulfone) bridge member. Particular preference is given to polyazo dyes containing the following bridge members: $-SO_2-NH-A^1-NH-SO_2-$, $-SO_2-N(Alk)-A^1-NH-SO_2-$ and $-SO_2-N(Alk)-A^1-N(Alk)-SO_2-$, where Alk and $A^1$ are each as defined in claim 1.

Preference is given to polyazo dyes of the formula I where $A^1$ is m- or p-phenylene with or without hydroxysulfonyl substitution.

The bridge member B attaches with each of its ends to the phenylene rings meta or para to the diazo group. Preference is given to polyazo dyes in which the two sites of attachment are para to the diazo group.

Polyazo dyes having at least one N-alkylated sulfonamide group in the bridge member are particularly preferred.

Preference is given particularly to dyes having the following 1,4-phenylene bridge members:

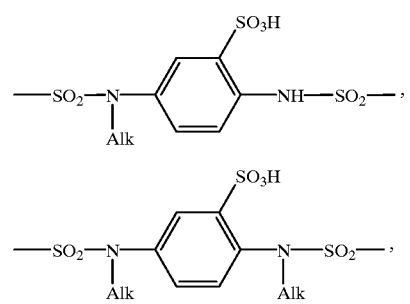

-continued

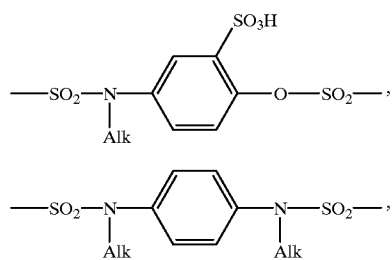

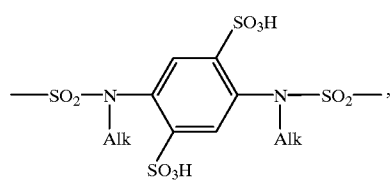

and also the 1,3-phenylene bridge members:

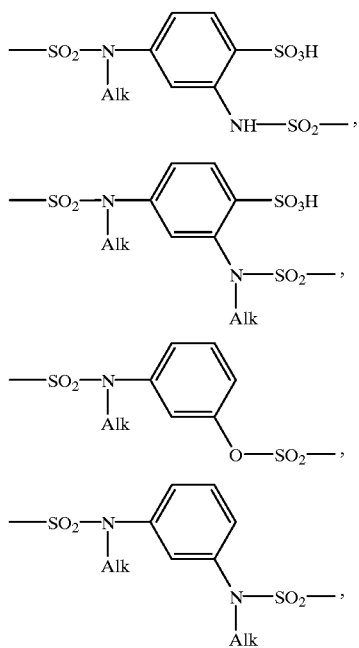

-continued

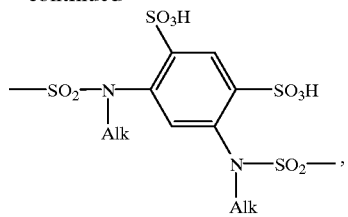

since their dyeings on cotton or wool have particularly good wetfastnesses.

Preference is given to polyazo dyes in which dyes derived from H-acid are linked together. Especially those of the general formula II (II)

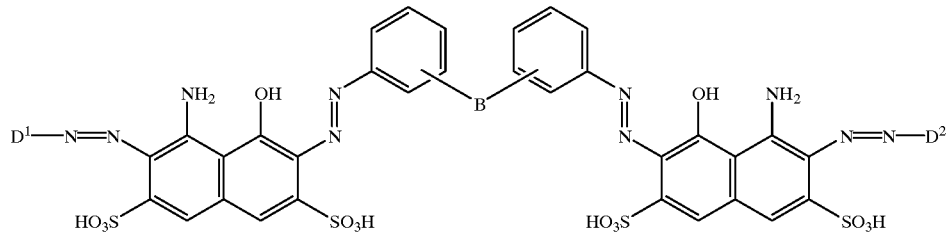

where $D^1$, $D^2$ and B are each as defined above.

Particular industrial interest here pertains to symmetrical polyazo dyes, i.e. polyazo dyes in which $D^1$ and $D^2$ are identical. $D^1$ and $D^2$ are each preferably a radical of the formula

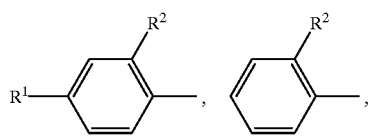

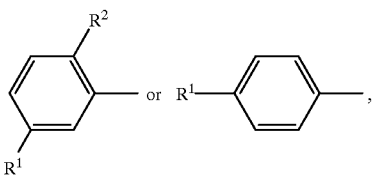

where $R^1$ and $R^2$ are each as defined above.

Very particularly important dyes have the general formulae IIIa–d

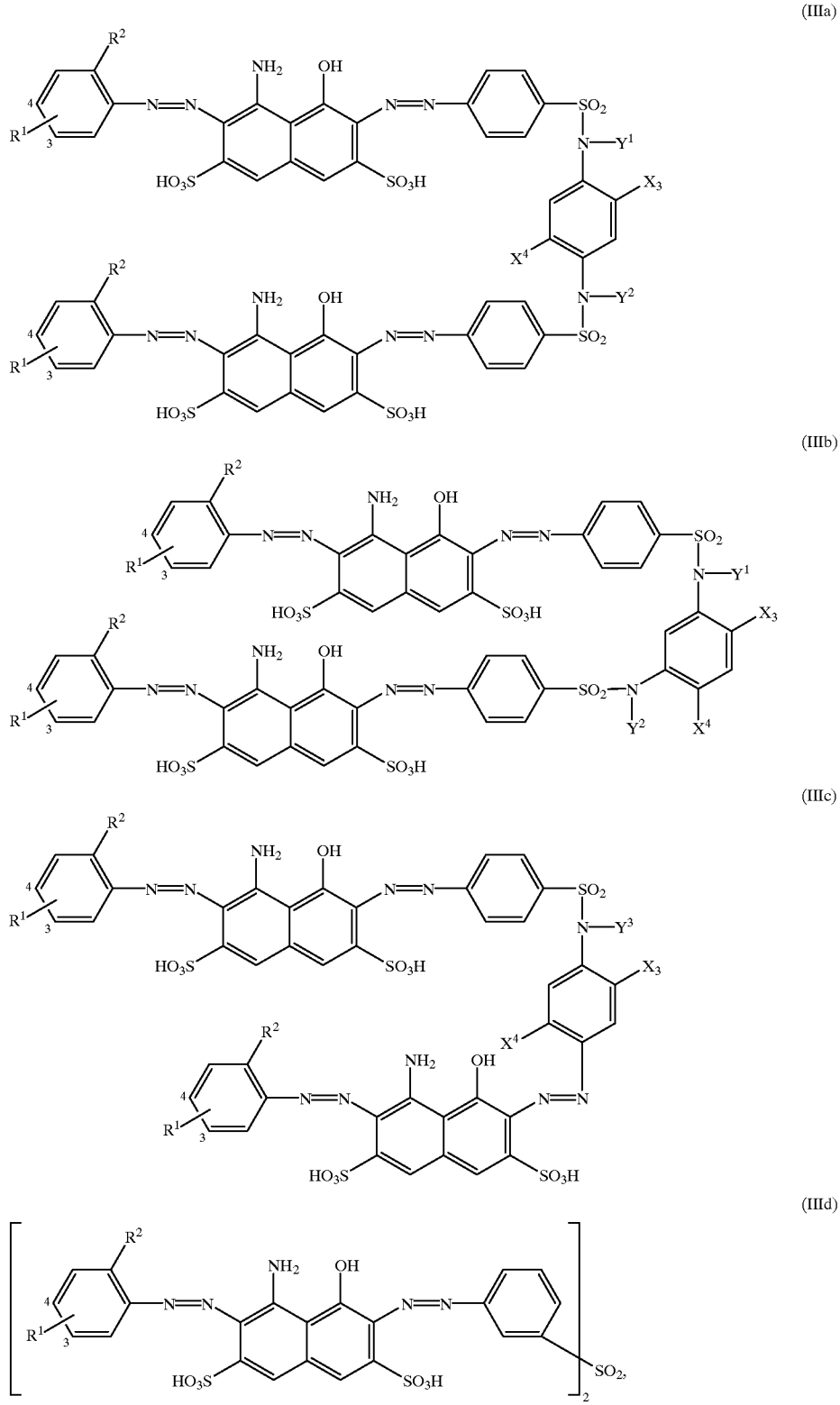
where
$R^1$ is hydrogen, nitro or a radical of the formula $HOC_2H_4SO_2$, $HO_3SOC_2H_4SO_2$, $CH_2=CH-$ $SO_2CH_2=CH-CH_2-SO_2$, CO—Ar, $SO_2$—Ar, $SO_2$—OAr, $SO_2$—N(Ar)Alk, $SO_2$—N(Alk)$_2$, CO—OAlk or CO—Alk,
$R^2$ is hydrogen, $C_1$–$C_4$-alkyl, $C_1$–$C_4$-alkoxy or a radical of the formula CO—OAlk, $Y^1$, $Y^2$ and $Y^3$ are each independently of the others $C_1$–$C_6$-alkyl with or without interruption by 1 or 2 oxygen atoms or 1 sulfonyl group and with or without hydroxyl, $C_1$–$C_4$-alkanoyloxy, sulfato, carboxyl or hydroxysulfonyl substitution, or $Y^1$ and/or $Y^2$ is hydrogen, $X^3$ and $X^4$ are each hydrogen or hydroxysulfonyl, $R^1$ is in position 3 or 4, and Alk and Ar are each as defined above.

Preferred radicals for $R^1$ in position 3 are the radicals of the formula $CO_2Alk$, $HOC_2H_4SO_2$ and $HO_3SOC_2H_4SO_2$.

In addition, preference is given to disazo dyes of the formula I in which the substituents are selected from a combination of the preferred substituents recited above.

The novel disazo dyes of the formula I are obtainable in a conventional manner.

For example, an aniline of the formula IV

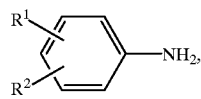

(IV)

where $R^1$ and $R^2$ are each as defined above, can be conventionally diazotized and coupled with a naphthalene of the formula V

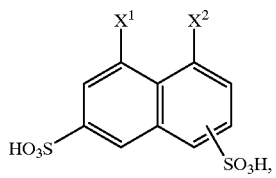

(V)

where $X^1$ and $X^2$ are each as defined above.

The resulting monoazo dye of the formula VI

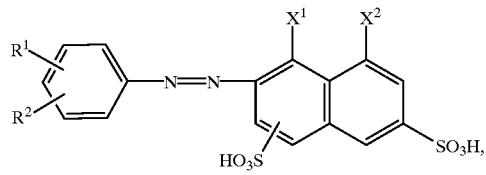

(VI)

can then be coupled with a tetrazonium salt derived from a bisamino compound of the formula VII

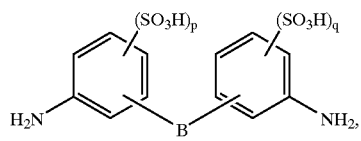

(VII)

where B, p and q are each as defined above.

The novel dyes of the formula I are advantageously useful for dyeing natural or synthetic substrates, for example cotton, wool, leather or polyamide.

The dyeings obtained have black and also blue to navy hues and good lightfastness and also good wetfastnesses.

The novel dyes can be applied not only alone but also mixed with each or one another or else mixed with other dyes.

The present invention further provides sulfonamides of the formula (VIIa)

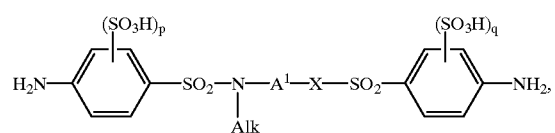

(VIIa)

where
p is 0 or 1,
q is 0 or 1,
$A^1$ is phenylene with or without hydroxysulfonyl substitution,
X is oxygen, imino or a radical

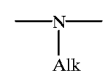

and
Alk is $C_1$–$C_8$-alkyl with or without interruption by from 1 to 3 oxygen atoms in ether function or by 1 sulfur atom or 1 sulfonyl group and with or without hydroxyl, $C_1$–$C_4$-alkanoyloxy, benzoyloxy, sulfato, halogen, cyano, carbamoyl, carboxyl, hydroxysulfonyl, phenyl or hydroxysulfonylphenyl substitution, or $C_5$–$C_8$-cycloalkyl.

The present invention further provides sulfonamides of the formula VIIb

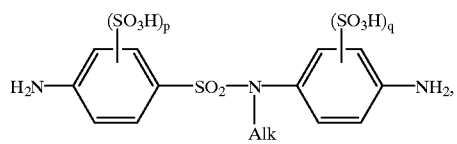

(VIIb)

where
p is 0 or 1,
q is 0 or 1 and
Alk is $C_1$–$C_8$-alkyl with or without interruption by from 1 to 3 oxygen atoms in ether function or by 1 sulfur atom or 1 sulfonyl group and with or without hydroxyl, $C_1$–$C_4$-alkanoyloxy, benzoyloxy, sulfato, halogen, cyano, carbamoyl, carboxyl, hydroxysulfonyl, phenyl or hydroxysulfonylphenyl substitution, or $C_5$–$C_8$-cycloalkyl.

Attention is drawn to the above observations for an exemplification of the Alk substituents.

The novel sulfonamides of the formula VIIa are obtainable in a conventional manner.

For example, an aniline of the formula VIII

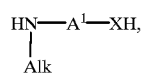

(VIII)

where Alk, $A^1$ and X are each as defined above, can be reacted twice with 4-acetylaminobenzenesulfonyl chloride to form the sulfonamide and then deacetylated.

The sulfonamides of the formula VIIb are accordingly obtainable by a single reaction of a nitroaminobenzene of the formula IX

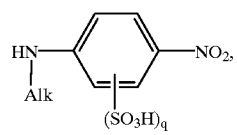

(IX)

with 4-acetylaminobenzenesulfonyl chloride and subsequent hydrogenation and deacetylation.

A further way to obtain the compounds of the formula VII*a* and VII*b* is alkylation of the imino group in the protected-amino, for example amino-acetylated, compounds of the formula X

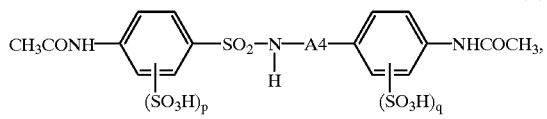

(X)

where $A^4$ is a direct bond or a bridge member of the formula $—A^1—X—SO_2—$, whose sulfonyl group is attached to the benzene ring. This alkylation, as is common knowledge, can be carried out in polar solvents such as water, acetone or alcohols in the alkaline pH range from 7 to 12 using alkylating agents such as dimethyl sulfate, diethyl sulfate or propanesultone. Removal of the protective groups leads to the compounds of the formulae VII*a* and VII*b*.

The intermediates not explicitly recited herein are well known and are obtainable in a way which is well known to one skilled in the art.

The Examples which follow illustrate the invention.

EXAMPLE 1 a) 281 g of the diazo component of the formula

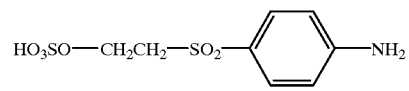

were dissolved in 1000 ml of water at pH 3.5 using about 85 g of sodium bicarbonate and then precipitated by subsequent addition of 227 ml of 36% strength by weight hydrochloric acid. The mixture was cooled down to 0° C. with ice and diazotized at temperatures below 5° C. by dropwise addition of 305 ml of aqueous 23% strength by weight sodium nitrite solution. After destruction of excess nitrous acid with amidosulfuric acid, the diazonium salt suspension was added to a hydrochloric-acid precipitation of 319 g of 1-amino-8-hydroxynaphthalene-3,6-disulfonic acid previously dissolved in 2200 ml of aqueous sodium hydroxide solution. The suspension was stirred at room temperature for 12 hours.

b) 108 g of 3,3'-diaminodiphenyl sulfone were stirred at room temperature in 600 ml of 18.5% strength by weight hydrochloric acid in 150 ml of water for one hour. The mixture was cooled down to temperatures below 0° C. and admixed with 310 ml of a 23% strength by weight sodium nitrite solution metered in over a period of 30–45 min. The mixture was subsequently stirred for one hour. The excess nitrous acid was destroyed and the solution adjusted to pH 2.0 with sodium bicarbonate. The resulting tetrazonium salt solution was added over 30 min to the dye solution prepared under a) and previously adusted to pH 7.0 with sodium carbonate. This gave a blue dye of the formula

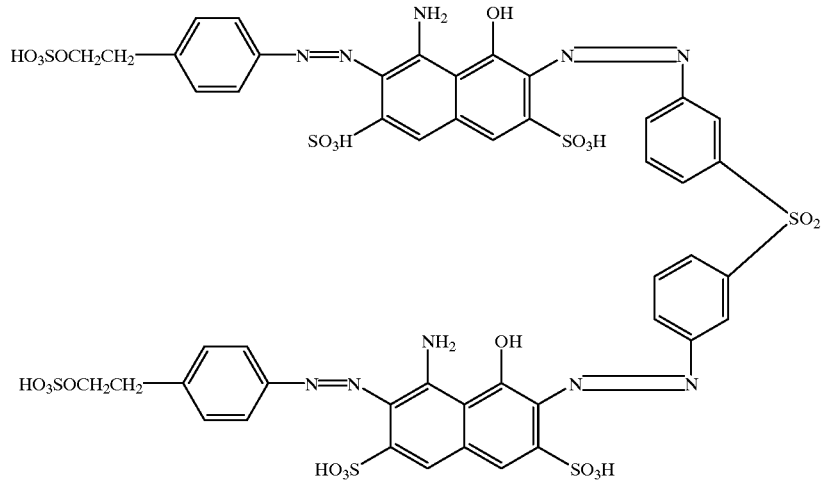

in the form of its free acid, which was simultaneously bound with sodium bicarbonate.

The pH of the coupling mixture was then adjusted to 6.0–6.3 using a little sodium phosphate, and the coupling solution was then concentrated by spray drying. This gave 1650 g of a bluish black powder which, applied to cotton by the exhaust method at 40–60° C., produced a deep navy having high wetfastnesses. $\lambda_{max}$ of the about 0.01% strength aqueous solution of about pH 4:586 nm.

EXAMPLE 2

Example 1 was repeated with 223 g of the compound of the formula

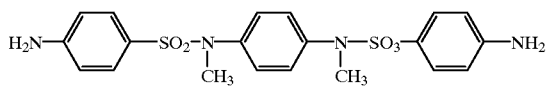

instead of 3,3-diaminodiphenyl sulfone, affording, after spray drying, the dye of the formula

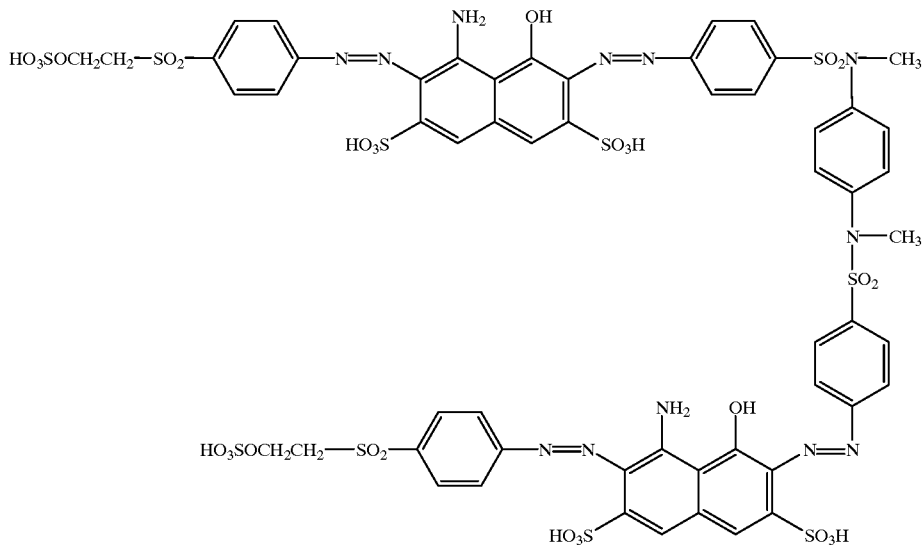

in the form of a black powder.

The ca. pH 4 solution of the dye in water had an absorption maximum at 583 nm.

The dye produces strong and wetfast navy shades on cotton.

EXAMPLE 3

209 g of the tetrazo component of the formula

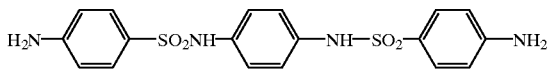

were stirred with 900 ml of 18.5% strength by weight hydrochloric acid for 12 h. The mixture was then cooled down to <0° C. with ice, and 305 ml of a 23% strength by weight aqueous sodium nitrite solution were added dropwise over 10 min. The resulting sand-colored suspension was diluted with 500 ml of cold water at 5° C. and subsequently stirred at about 5° C. for 1 h. Excess nitrous acid was then destroyed, and the suspension was metered into 468 g of the coupling component of the formula

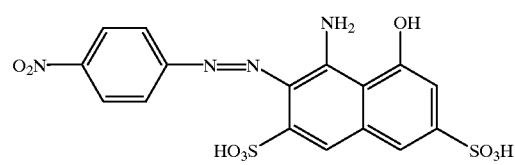

previously dissolved in 2000 ml of water at pH 7–8. At the same time the coupling pH was maintained within the range from 6.5 to 9 using sodium carbonate. The mixture was then stirred at pH 8.5 for 40 min, thereafter acidified with hydrochloric acid at pH 4.5 and admixed with sodium chloride at 80° C.

The dye of the formula

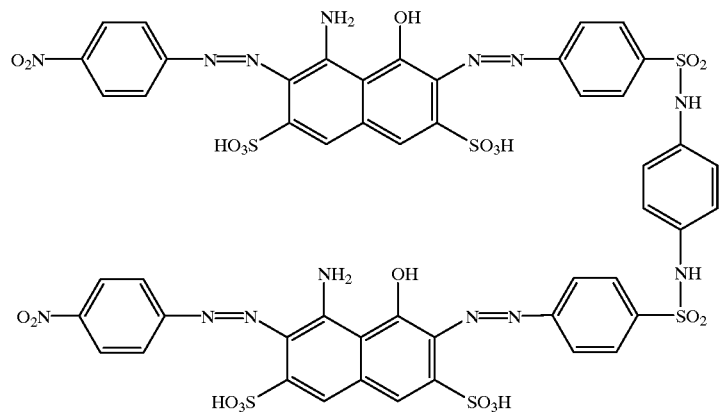

was obtained in a readily filterable form as sodium salt. Filtration with suction and drying afforded 1220 g of a black powder which formed a reddish blue solution in water. $\lambda_{max}$(pH=4):560 nm (shoulder at about 620 nm).

The dye produced blue to deep navy shades having excellent wetfastnesses on polycaprolactam fabric.

EXAMPLE 4

Example 3 was repeated using 563 g of the coupling component of the formula

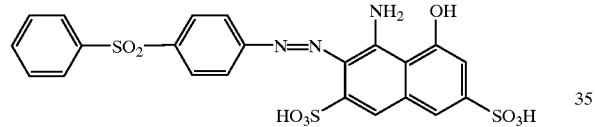

prepared by acidic coupling of the diazonium salt diphenyl sulfone 4-diazonium chloride onto 1-amino-8-hydroxynaphthalene-3,6-disulfonic acid at pH <2.

Isolation of the dye as described in Example 3 afforded a black powder of the formula

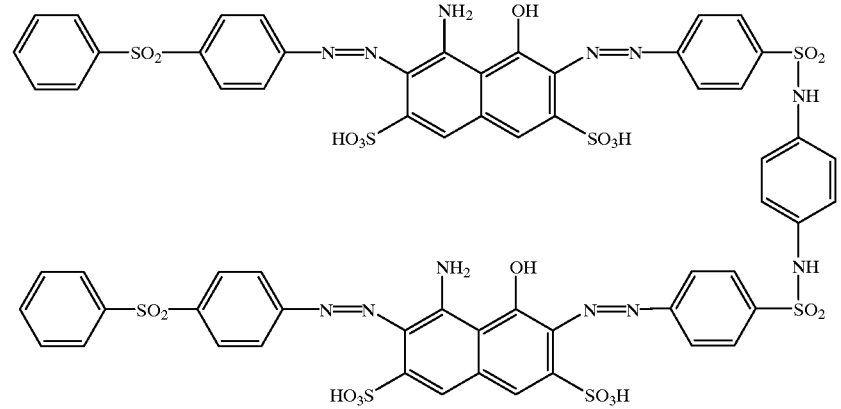

The dye formed a reddish blue solution in water and produced a fast navy shade on polycaprolactam fabric.

The method of Example 2 was also used to obtain the following dyes:
EXAMPLE 5
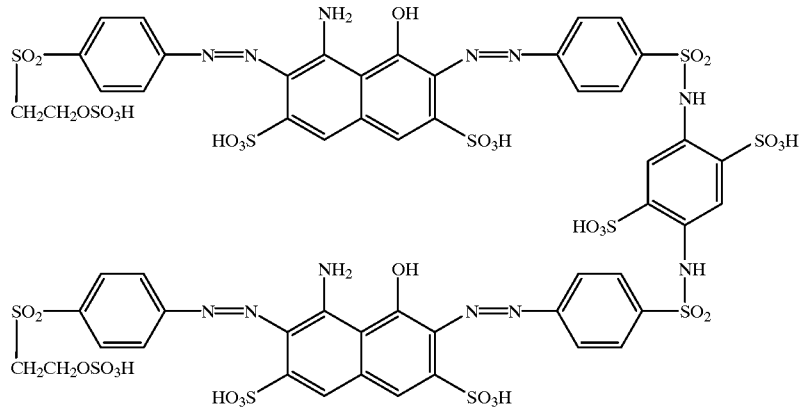
The dye produces a navy shade on cotton.
EXAMPLE 6
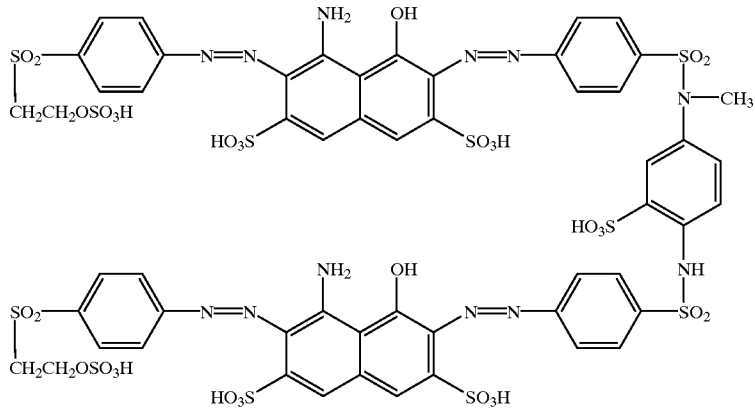
The dye produces a navy shade on cotton.
EXAMPLE 7
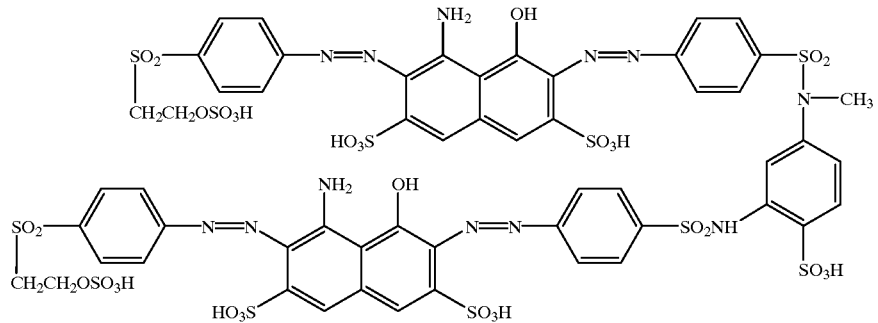

The dye produces a navy shade on cotton.
EXAMPLE 8
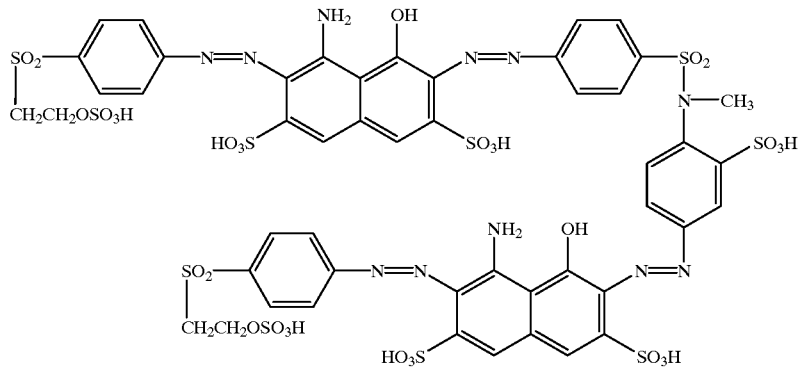
The dye produces a blackish navy shade on cotton.
EXAMPLE 9
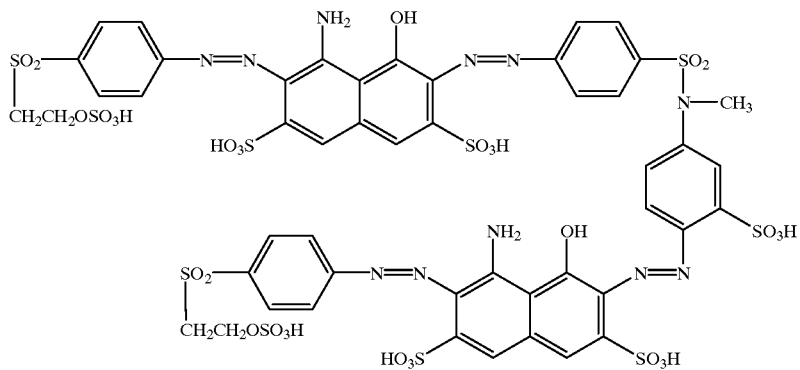
The dye produces a blackish navy shade on cotton.
EXAMPLE 10
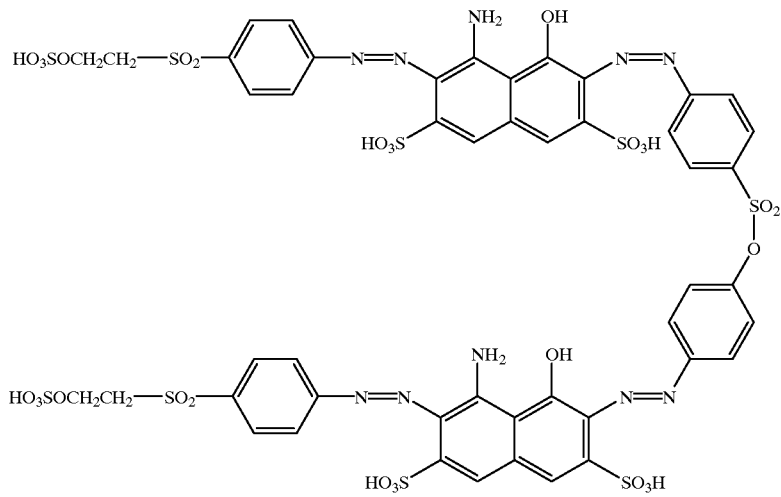
The dye produces a bluish black shade on cotton ($\lambda_{max}$=600 nm broad).
The methods of Examples 2, 3 and 4 were also used to obtain the dyes specificized in the following tables:

TABLE 1

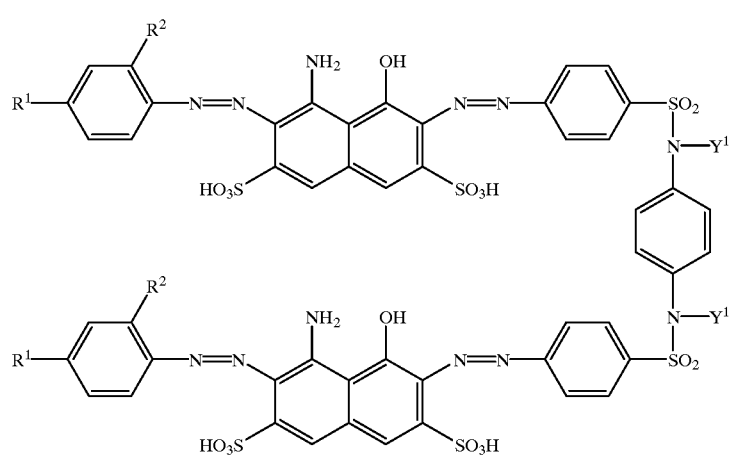

| Ex. No. | R¹ | R² | Y¹ | Hue |
|---|---|---|---|---|
| 1.1 | H | CO₂CH₃ | H | blue |
| 1.2 | H | CO₂CH₃ | CH₃ | blue |
| 1.3 | CH₃O₂C— | H | H | blue |
| 1.4 | CH₃O₂C— | H | CH₃ | blue |
| 1.5 | H | CO₂CH₃ | C₂H₅ | blue |
| 1.6 | H | CO₂C₂H₅ | H | blue |
| 1.7 | H | CO₂C₂H₅ | CH₃ | blue |
| 1.8 | H | CO₂C₂H₅ | C₂H₅ | blue |
| 1.9 | C₆H₅—SO₂— | H | CH₃ | blue |
| 1.10 | C₆H₅OSO₂— | H | H | blue |
| 1.11 | C₆H₅OSO₂— | H | CH₃ | blue |
| 1.12 | C₆H₅CO— | H | H | blue |
| 1.13 | C₆H₅CO— | H | CH₃ | blue |
| 1.14 | CH₃—C₆H₄—CO— | H | H | blue |
| 1.15 | 2,4-(CH₃)₂—C₆H₃—CO— | H | H | blue |
| 1.16 | NO₂ | H | CH₃ | blue |
| 1.17 | (CH₃)₂N—SO₂— | H | H | blue |
| 1.18 | (CH₃)₂N—SO₂— | H | CH₃ | blue |
| 1.19 | (CH₃)₂N—SO₂— | H | H | blue |
| 1.20 | (HOC₂H₅)(C₂H₅)N—SO₂— | H | CH₃ | blue |
| 1.21 | (CH₃OCH₂CH₂)(C₂H₅)N—SO₂— | H | H | blue |
| 1.22 | (CH₃OCH₂CH₂)(C₂H₅)N—SO₂— | H | CH₃ | blue |
| 1.23 | (CH₃)₂N—CO— | H | H | blue |
| 1.24 | CH₃NH—CO— | H | CH₃ | blue |
| 1.25 | n—C₄H₉NH—CO— | H | H | blue |
| 1.26 | n—C₄H₉NH—CO— | H | CH₃ | blue |

TABLE 1-continued

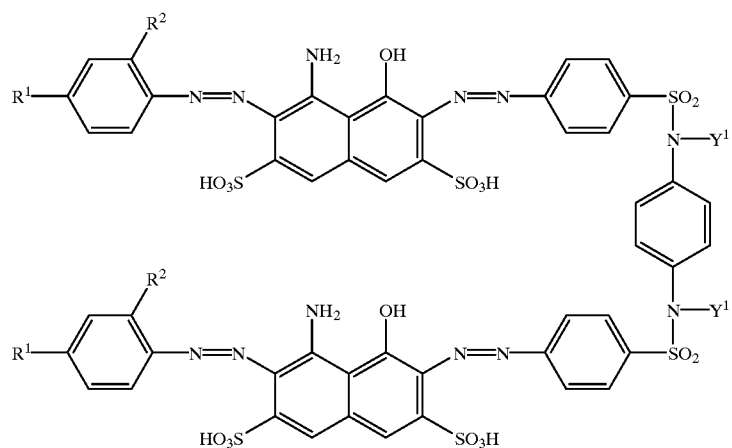

| Ex. No. | R¹ | R² | Y¹ | Hue |
|---|---|---|---|---|
| 1.27 | CH₃—C₆H₄—SO₂— | H | H | blue |
| 1.28 | CH₃—C₆H₄—SO₂— | H | CH₃ | blue |
| 1.29 | CH₂=CH—SO₂— | H | CH₃ | blue |
| 1.30 | CH₂=CH—SO₂— | H | C₂H₅ | blue |
| 1.31 | C₄H₉(n)—SO₂— | H | H | blue |
| 1.32 | C₄H₉(n)—SO₂— | H | CH₃ | blue |

TABLE 2

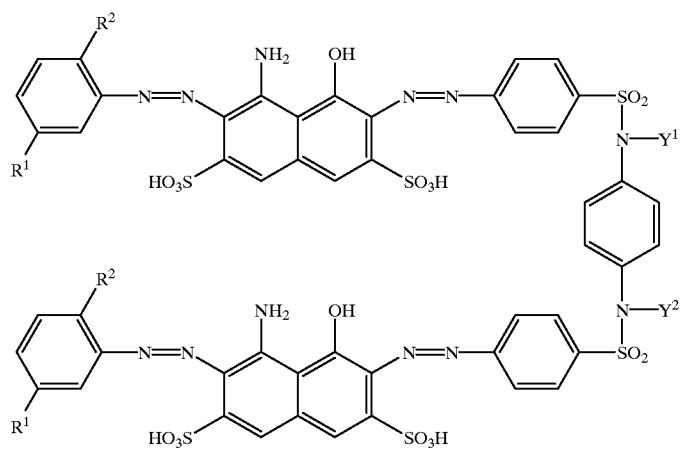

| Ex. No. | R¹ | R² | Y¹ | Y² | Hue |
|---|---|---|---|---|---|
| 2.1 | CO₂CH₃ | CO₂CH₃ | H | H | blue |
| 2.2 | CO₂CH₃ | CO₂CH₃ | CH₃ | H | blue |
| 2.3 | CO₂CH₃ | CO₂CH₃ | C₂H₅ | H | blue |
| 2.4 | CO₂CH₃ | CO₂CH₃ | CH₃ | CH₃ | blue |
| 2.5 | CO₂CH₃ | H | CH₃ | H | blue |
| 2.6 | CO₂CH₃ | H | H | H | blue |
| 2.7 | (C₂H₅)₂N—SO₂ | H | H | H | blue |
| 2.8 | (C₂H₅)₂N—SO₂ | H | CH₃ | H | blue |
| 2.9 | HOC₂H₄SO₂ | H | CH₃ | H | blue |
| 2.10 | HO₃SOCH₂CH₂SO₂ | H | CH₃ | CH₃ | navy |

TABLE 2-continued

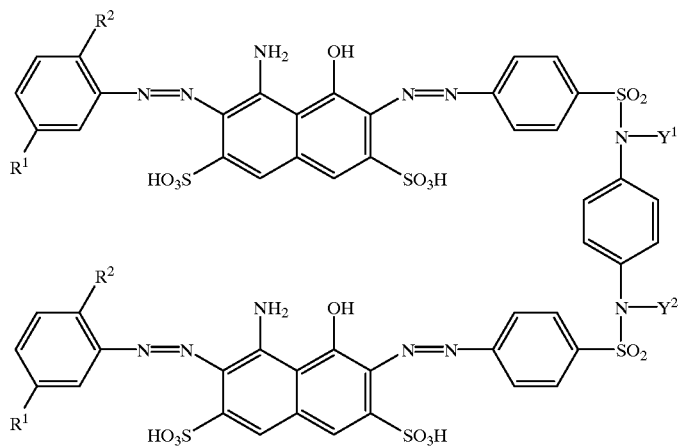

| Ex. No. | $R^1$ | $R^2$ | $Y^1$ | $Y^2$ | Hue |
|---|---|---|---|---|---|
| 2.11 | $HO_3SOCH_2CH_2SO_2$ | $SO_3H$ | $CH_3$ | $CH_3$ | blue |
| 2.12 | $CO_2CH_2CH_3$ | $CO_2CH_2CH_3$ | H | H | blue |
| 2.13 | $CO_2CH_3$ | H | $CH_3$ | $CH_3$ | blue |

TABLE 3

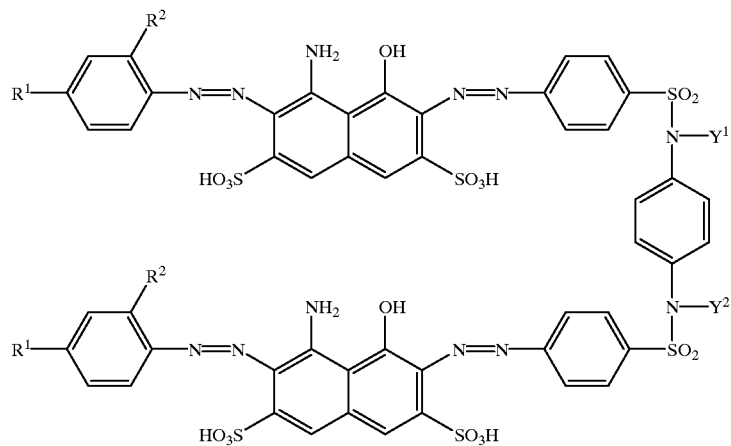

| Ex. No. | $R^1$ | $R^2$ | $Y^1$ | $Y^2$ | Hue |
|---|---|---|---|---|---|
| 3.1 | $NO_2$ | H | $CH_3$ | H | blue |
| 3.2 | $NO_2$ | H | $C_2H_5$ | H | blue |
| 3.3 | $C_6H_5SO_2$ | H | $CH_3$ | H | blue |
| 3.4 | $C_6H_5SO_2$ | H | $C_2H_5$ | H | blue |
| 3.5 | $(C_2H_5)N-SO_2$ | H | $CH_3$ | H | blue |
| 3.6 | $CH_3CO$ | H | H | H | blue |
| 3.7 | $CH_3CO$ | H | $CH_3$ | H | blue |
| 3.8 | $C_2H_5CO$ | H | H | H | blue |
| 3.9 | $C_2H_5$ | H | $CH_3$ | $CH_3$ | blue |
| 3.10 | $HO_3SOCH_2CH_2SO_2$ | H | $CH_3$ | $CH_3$ | navy |
| 3.11 | $HO_3SOCH_2CH_2SO_2$ | H | H | $CH_3$ | navy |
| 3.12 | $NO_2$ | H | H | H | blue |
| 3.13 | $NO_2$ | H | $CH_3$ | $CH_3$ | blue |
| 3.14 | H | $CH_3O_2C$ | H | H | blue |
| 3.15 | H | $CH_3O_2C$ | $CH_3$ | H | blue |
| 3.16 | H | $CH_3O_2C$ | $CH_3$ | $CH_3$ | blue |
| 3.17 | $C_6H_5SO_2$ | H | H | H | blue |
| 3.18 | $C_6H_5SO_2$ | H | $CH_3$ | H | blue |

TABLE 3-continued
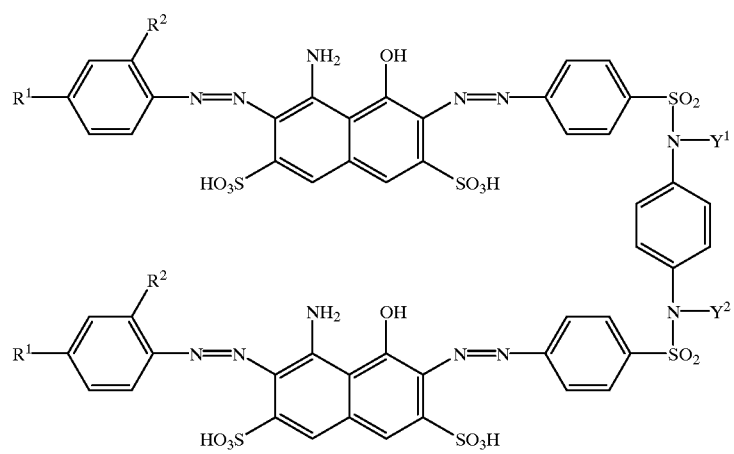
| Ex. No. | $R^1$ | $R^2$ | $Y^1$ | $Y^2$ | Hue |
|---|---|---|---|---|---|
| 3.19 | $C_6H_5SO_2$ | H | $CH_3$ | $CH_3$ | blue |
TABLE 4
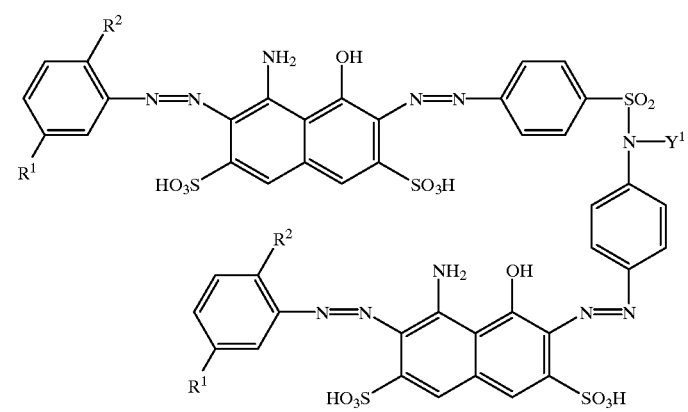
| Ex. No. | $R^1$ | $R^2$ | $Y^1$ | Hue |
|---|---|---|---|---|
| 4.1 | $HO_3SOCH_2CH_2SO_2$ | H | $CH_3$ | bluish navy |
| 4.2 | $HO-CH_2CH_2SO_2$ | H | $CH_3$ | blue |
| 4.3 | $HO_3SOCH_2CH_2SO_2$ | H | $C_2H_5$ | bluish navy |
| 4.4 | $CH_3O_2C$ | $CH_3O_2C$ | $CH_3$ | bluish navy |
| 4.5 | $CH_3O_2C$ | $CH_3O_2C$ | $C_2H_5$ | bluish navy |

TABLE 5

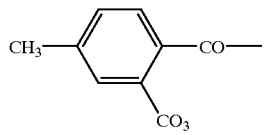

| Ex. No. | R¹ | R² | Y¹ | Hue, ($\lambda_{max}$ nm) |
|---|---|---|---|---|
| 5.1 | $HO_3SOCH_2CH_2SO_2$ | H | $CH_3$ | bluish navy, 597 |
| 5.2 | $HO_3SOCH_2CH_2SO_2$ | H | $C_2H_5$ | navy, 598 |
| 5.3 | $HO_3SOCH_2CH_2SO_2$ | H | $CH_2CH_2CH_2SO_3H$ | blackish navy |
| 5.4 | $NO_2$ | H | $CH_3$ | navy, 581 |
| 5.5 | $NO_2$ | H | $C_2H_5$ | navy, 581 |
| 5.6 | $CH_3O_2C$ | H | $CH_3$ | bluish navy, |
| 5.7 | $CH_3O_2C$ | H | $C_2H_5$ | bluish navy |
| 5.8 | H | $CH_3O_2C$ | $CH_3$ | blue |
| 5.9 | H | $CH_3O_2C$ | $C_2H_5$ | blue |
| 5.10 | $C_6H_5SO_2$ | H | $CH_3$ | navy |
| 5.11 | $C_6H_5SO_2$ | H | $C_2H_5$ | navy |
| 5.12 | 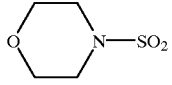 | H | $CH_3$ | bluish navy |
| 5.13 | (morpholine-N-SO₂) | H | $CH_3$ | blue |
| 5.14 | $HO_3SOCH_2CH_2SO_2$ | H | $CH_2CH_2CH_2OH$ | blackish navy |
| 5.15 | $HO_3SOCH_2CH_2SO_2$ | H | $CH_2CH_2OH$ | blackish navy |
| 5.16 | $HO_3SOCH_2CH_2SO_2$ | H | $C_2H_4SO_2C_2H_4OSO_3H$ | black |
| 5.17 | $HO_3SOCH_2CH_2SO_2$ | H | $C_2H_4SO_2C_2H_4OCOCH_3$ | black |

TABLE 6

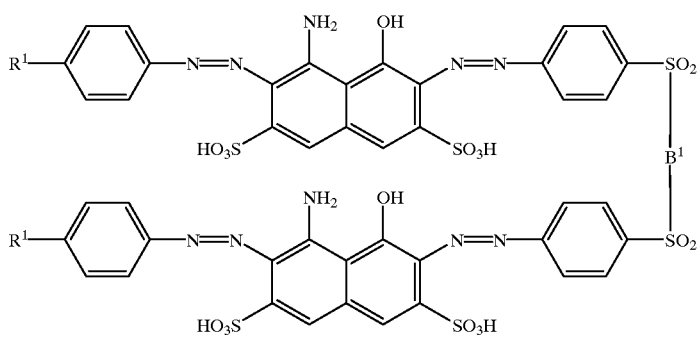

| Ex. No. | A | B¹ | Hue |
|---|---|---|---|
| 6.1 | $HO_3S-OCH_2CH_2SO_2-$ | —O—C₆H₄—O— (para) | navy $\lambda_{max}$ = 576 nm |
| 6.2 | $H_2C=CH-SO_2-$ | —O—C₆H₄—O— (para) | navy |
| 6.3 | $HO_3S-OCH_2CH_2SO_2-$ | —O—C₆H₄—N(CH₃)— (para) | blackish navy $\lambda_{max}$ = 581 nm |
| 6.4 | $H_2C=CH-SO_2-$ | —O—C₆H₄—N(CH₃)— (para) | blackish navy |
| 6.5 | $HO_3S-OCH_2CH_2SO_2-$ | —O—C₆H₄—O— (meta) | navy $\lambda_{max}$ = 574 nm |
| 6.6 | $H_2C=CH-SO_2-$ | —O—C₆H₄—O— (meta) | navy |
| 6.7 | $HO_3S-OCH_2CH_2SO_2-$ | —O—C₆H₃(CH₃)—N— (meta) | blackish navy |

EXAMPLE 11

188 g of 1,4-diaminobenzene-2-sulfonic acid (calculated at 100%) were dissolved in 1900 ml of water at pH 7 using aqueous sodium hydroxide solution. The solution was heated to 50° C. and admixed with 450 g of ground p-acetaminobenzenesulfonyl chloride (calculated at 100%) added a little at a time over 1 hour with vigorous stirring, simultaneously with first 25 g of sodium carbonate and then 25% strength by weight aqueous sodium hydroxide solution in such a way that the pH of the mixture was initially 7–8 and later, after about 50% of the sulfonyl chloride had been added, within the range from 7.5 to 8.5. The resulting suspension was then additionally stirred at 50° C. for 1 hour. Thereafter the pH of the mixture was adjusted to 10.5 with aqueous sodium hydroxide solution. 138 g of dimethyl sulfate were then added dropwise over 30 min while the pH of the mixture was maintained at 10–11 using aqueous sodium hydroxide solution. The mixture was subsequently stirred at 40–50° C. for 30 min, 20 g of 25% strength by weight aqueous ammonia solution were added, the mixture was adjusted to pH 14 with 50% strength by weight sodium hydroxide solution, and a deacetylation was carried out at 90–95° C. at a pH of 13–14 over 7 h. For this purpose, a total of about 170 g of 50% strength by weight aqueous sodium hydroxide solution were added subsequently. The mixture was then allowed to cool down and was neutralized with 18.5% strength by weight hydrochloric acid. The resulting colorless precipitate of the formula

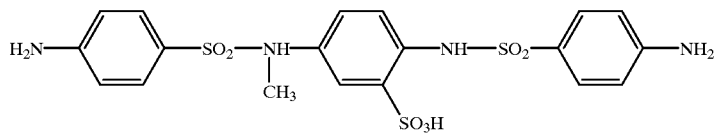

was filtered off with suction at pH 6–7 and washed with cold water, affording 480 g of a colorless powder.

EXAMPLE 12

Example 11 was repeated with the 1,4-diaminobenzene-2-sulfonic acid replaced by 244 g of the compound of the formula

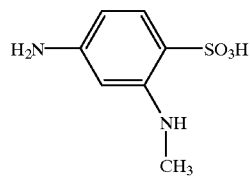

and deacetylation at pH>12 and subsequent neutralization, affording similarly to Example 11 500 g of the tetrazo component of the formula

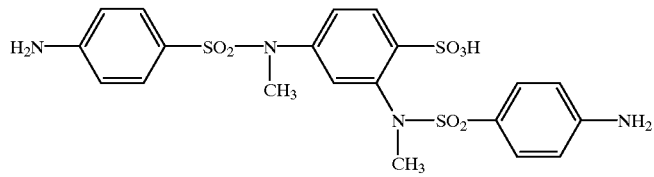

We claim:

1. A polyazo dye of the formula I

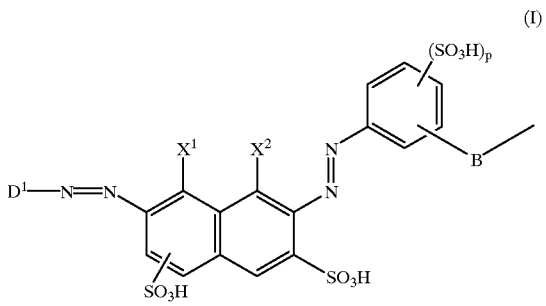

-continued

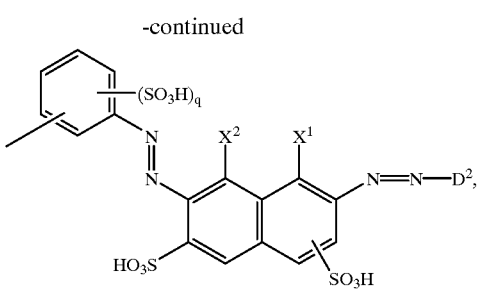

where one of the two radicals $X^1$ and $X^2$ is hydroxyl and the other is amino, p is 0 or 1, q is 0 or 1, $D^1$ and $D^2$ are each independently of the other a radical of the formula

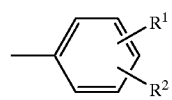

B is a bridge member of the formula
—$SO_2$—NH—$A^1$—NH—$SO_2$—, —$SO_2$—N(Alk)—$A^1$—NH—$SO_2$—,
—$SO_2$—N(Alk)—$A^1$—N(Alk)—$SO_2$—, —$SO_2$—N(Alk)—$A^1$—O—$SO_2$—, —SO$_2$—O—A$^1$—O—SO$_2$—, —SO$_2$—N(Alk)—, —SO$_2$—N(Alk)—SO$_2$—, —SO$_2$—NH—A$^2$—NH—SO$_2$— or SO$_3$—, where A$^1$ is phenylene with or without substitution by hydroxysulfonyl, A$^2$ is C$_1$–C$_8$-alkylene, and R$^1$ is hydrogen, C$_1$–C$_4$-alkyl, halogen, cyano, nitro, hydroxysulfonyl, pyrrolidinylsulfonyl, piperidinylsulfonyl, morpholinylsulfonyl or a radical of the formula CO—Ar, CO—OAr, CO—Alk, CO—OAlk, CO—N(Ar)Alk, CO—N(Alk)$_2$, SO$_2$—Ar, SO$_2$—Alk, SO$_2$—CH$_2$CH=CH$_2$, SO$_2$—CH=CH$_2$, SO$_2$—C$_2$H$_4$—Q, SO$_2$—OAr, SO$_2$—N(Alk)$_2$, SO$_2$—NHAlk, SO$_2$—N(Ar)Alk, SO$_2$—NHAr,

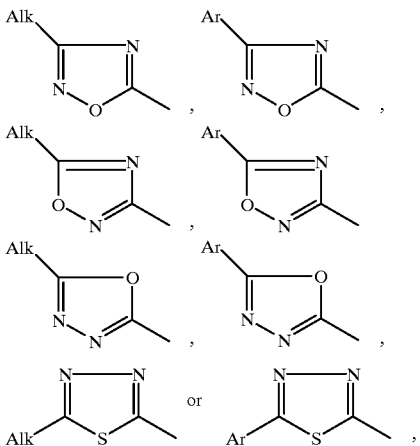

Alk is C$_1$–C$_8$-alkyl with or without interruption by from 1 to 3 oxygen atoms in ether function or by 1 sulfur atom or one sulfonyl group and with or without hydroxyl, C$_1$–C$_4$-alkanoyloxy, benzoyloxy, sulfato, halogen, cyano, carbamoyl, carboxyl, hydroxysulfonyl, phenyl or hydroxysulfonylphenyl substitution, or C$_5$–C$_8$-cycloalkyl, Ar is phenyl or naphthyl, these radicals each being with or without substitution by C$_1$–C$_4$-alkyl, halogen, C$_1$–C$_4$-alkoxy, phenoxy, hydroxyl, carboxyl, C$_1$–C$_4$-alkanoylamino whose alkyl chain is with or without interruption by one oxygen atom in ether function, benzoylamino, hydroxysulfonyl, pyrrolidinylsulfonyl, piperidinylsulfonyl, morpholinylsulfonyl or a radical of the formula SO$_2$—Alk, SO$_2$—CH$_2$CH=CH$_2$, SO$_2$—CH=CH$_2$, SO$_2$—C$_2$H$_4$—Q, SO$_2$—NHAlk, SO$_2$—N(Alk)$_2$, SO$_2$—G, SO$_2$—OG, SO$_2$—NHG or SO$_2$—N(Alk)G, R$^2$ is hydrogen, hydroxysulfonyl, C$_1$–C$_4$-alkyl, C$_1$–C$_4$-alkoxy or a radical of the formula CO—Ar, CO—OAlk, CO—OAr, SO$_2$—Ar, SO$_2$—Alk, SO$_2$—OAr,

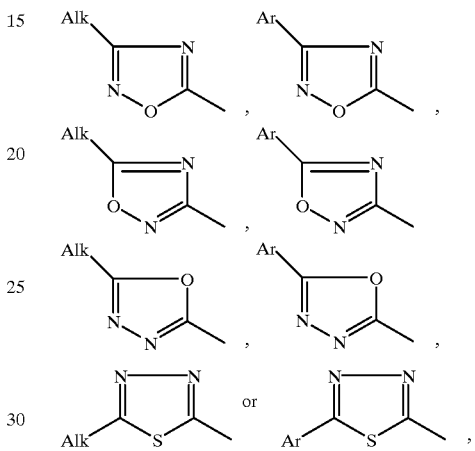

Q is hydroxyl or an alkali-detachable group, and

G is phenyl with or without C$_1$–C$_4$-alkyl, carboxyl, hydroxysulfonyl or C$_1$–C$_4$-alkanoylamino substitution, or naphthyl with or without hydroxysulfonyl substitution.

2. The polyazo dye as claimed in claim 1, wherein B is a bridge member of the formula —SO$_2$—NH—A$^1$—NH—SO$_2$—, —SO$_2$—N(Alk)—A$^1$—NH—SO$_2$—or —SO$_2$—N(Alk)—A$^1$—N(Alk)—SO$_2$—, where Alk and A$^1$ are each as defined in claim 1.

3. The polyazo dye as claimed in claim 1 or 2, wherein A$^1$ is m- or p-phenylene with or without hydroxysulfonyl substitution.

4. The polyazo dye as claimed in claim 1, wherein p and q are each 0.

5. The polyazo dye as claimed in claim 1, wherein the bridge member B attaches to both phenyl rings para to the diazo group.

6. The polyazo dye as claimed in claim 1, to which the formula II

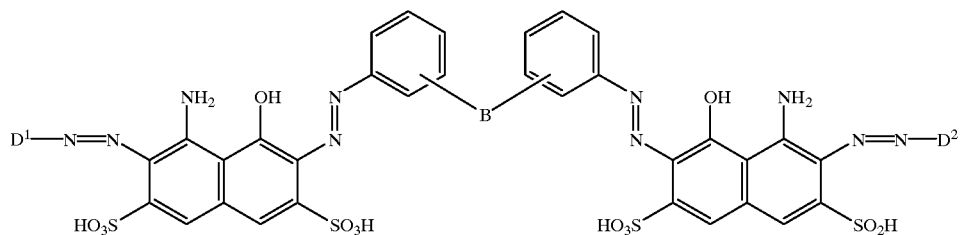

applies, where B, $D^1$ and $D^2$ are each as defined in claim 1.

7. The polyazo dye as claimed in claim 1, wherein Alk is $C_1$–$C_6$-alkyl with or without interruption by one or two oxygen atoms in ether function or by one sulfonyl group and with or without hydroxyl, $C_1$–$C_4$-alkanoyloxy, sulfato, chlorine, cyano, carboxyl, hydroxysulfonyl, phenyl or hydroxysulfonyl-phenyl substitution.

8. The polyazo dye as claimed in claim 1, wherein Ar is phenyl with or without substitution by $C_1$–$C_4$-alkoxy, carboxyl, $C_1$–$C_4$-alkanoylamino, methoxyacetylamino, hydroxysulfonyl or a radical of the formula $SO_2$—$CH=CH_2$, $SO_2$—$C_2H_4$—Q, $SO_2$—NHAlk, $SO_2$—N(Alk)$_2$, $SO_2$—G, $SO_2$—OG, $SO_2$—NHG or $SO_2$—N(Alk)G, where Q, Alk and G are each as defined in claim 1.

9. The polyazo dye as claimed in claim 1, wherein $D^1$ and $D^2$ are each a radical to which the formula

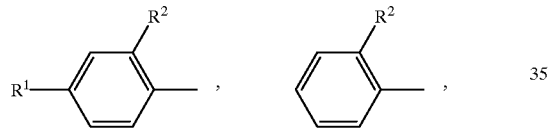

-continued

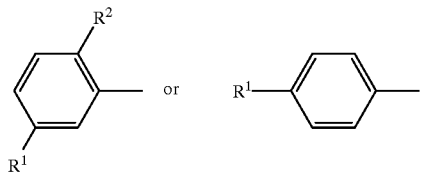

applies, where $R^1$ and $R^2$ are each as defined in claim 1.

10. A method for dyeing a natural or synthetic substrate comprising applying a diazo dye of claim 1 to said substrate in dyeing-effective amounts.

* * * * *